United States Patent [19]
Cote, Sr.

[11] Patent Number: 5,775,671
[45] Date of Patent: Jul. 7, 1998

[54] LUER-ACTIVATED VALVE

[75] Inventor: Andrew L. Cote, Sr., Merrimack, N.H.

[73] Assignee: Nypro Inc., Clinton, Mass.

[21] Appl. No.: 751,357

[22] Filed: Nov. 18, 1996

Related U.S. Application Data

[63] Continuation-in-part of Ser. No. 662,616, Jun. 13, 1996, abandoned.

[51] Int. Cl.$^6$ ............................................. F16K 15/14
[52] U.S. Cl. .................................. 251/149.8; 251/149.1
[58] Field of Search ........................... 251/149.8, 149.1; 604/167, 256

[56] References Cited

U.S. PATENT DOCUMENTS

| | | |
|---|---|---|
| 3,192,949 | 7/1965 | De See . |
| 3,570,484 | 3/1971 | Steer et al. . |
| 4,387,879 | 6/1983 | Tauschinski . |
| 4,429,856 | 2/1984 | Jackson . |
| 4,683,916 | 8/1987 | Raines . |
| 4,842,591 | 6/1989 | Luther ........................ 604/167 X |
| 5,190,067 | 3/1993 | Paradis et al. ............... 251/149.1 X |
| 5,390,898 | 2/1995 | Smedley et al. . |
| 5,456,675 | 10/1995 | Wolbring et al. ............ 604/256 X |
| 5,465,938 | 11/1995 | Werge et al. ............... 251/149.1 |
| 5,535,785 | 7/1996 | Werge et al. . |
| 5,540,661 | 7/1996 | Tomisaka et al. . |

*Primary Examiner*—Kevin Lee
*Attorney, Agent, or Firm*—Bromberg & Sunstein LLP

[57] ABSTRACT

A normally closed valve that may be opened upon insertion of a nozzle, wherein an actuator that engages the nozzle is shaped to enhance the ability to flush thoroughly the interior volume of the valve, which includes a valving chamber. Located in the valving chamber is an actuateable valve element that, in a first position, blocks flow through the passageway passing through the housing and that, in a second position, permits flow through the passageway. The actuator, which has a perimeter wall, is disposed adjacent the actuateable valve element. The inlet end of the actuator engages the nozzle when the nozzle is inserted into the valve, and the actuator urges the actuateable valve element into the second position when the nozzle pushes on the actuator. The perimeter wall may define an interior actuator path passing through the inside of the actuator. An exterior actuator path passes between the perimeter wall and the housing. The actuator includes structures for permitting flow from the nozzle to the exterior actuator path, and in a preferred embodiment, structures disposed on the perimeter wall's outlet end permit flow from the interior actuator path to the valving chamber. The actuator preferably further includes a structure, disposed within the perimeter wall, for restricting flow through the interior actuator path. This structure for restricting flow preferably includes a transverse wall mounted to and within the perimeter wall. Protrusions on the exterior of the perimeter wall may be used to keep the actuator centered in the valve.

44 Claims, 12 Drawing Sheets

LUER-ACTIVATED VALVE

RELATED APPLICATION

The present application is a continuation-in-part of U.S. patent application Ser. No. 08/662,616, filed Jun. 13, 1996, now abandoned, which is incorporated herein by reference.

TECHNICAL FIELD

The present invention relates to valves that may be actuated by nozzles and in particular by male Luer fittings.

BACKGROUND ART

Many prior-art Luer-activated valves use an actuator, located in the inlet passage upstream of a valve element, for separating a valve element from a valve seat upon engagement by a Luer tip. In many cases, the actuator is hollow, and most of the fluid flowing through the valve passes through the hollow interior of the actuator. With little or no flow around the exterior of the actuator, the space between the actuator and the inner surface of the inlet passage may not get properly flushed out each time fluid is injected into or aspirated from the valve. This problem could be of concern, for example, when the valve is used repeatedly to draw blood from a patient or to transfuse blood to a patient. The blood may become trapped between the actuator and the inner surface of the inlet passage and, upon exposure to the atmosphere, may coagulate.

SUMMARY OF THE INVENTION

The present invention is directed to a normally closed valve that may be opened upon insertion of a nozzle, which in a preferred embodiment is a male Luer fitting, and in particular is directed to an improved actuator used in such a valve for actuating a valve element. The use of the improved actuator in the valve enhances the ability of the user to flush thoroughly the interior volume of the valve.

The valve includes a housing, which has an inlet housing portion defining an inlet section of a fluid passageway and an outlet housing portion defining an outlet section of the fluid passageway. The inlet section is shaped to receive the nozzle. The inner diameter of the inlet section is preferably tapered as a female Luer fitting, so that a tight seal may be formed between the outer diameter of a male Luer fitting and the inner diameter of the inlet section of the passageway. The inlet and outlet housing portions are connected so as to permit fluid communication between the inlet and outlet sections of the fluid passageway. The housing also defines a valving chamber, which forms a section of the fluid passageway between the inlet section and the outlet section.

Located in the valving chamber is an actuateable valve element that, in a first position, blocks flow through the passageway and that, in a second position, permits flow through the passageway. The actuateable valve element preferably includes a flexible, resilient disk. In a preferred embodiment, the actuateable valve element, in the first position, rests against the valve's valve seat and, in the second position, is spaced away from the valve seat. Preferably, the valve includes a central support for urging the flexible, resilient disk against the valve seat.

An actuator is disposed adjacent the actuateable valve element and the inlet section. The actuator includes a perimeter wall, which has inlet and outlet ends respectively disposed away from and towards the valve element. The inlet end of the actuator engages the nozzle when the nozzle is inserted into the inlet section, and the actuator urges the actuateable valve element into the second position when the nozzle pushes on the actuator. A flow path—an exterior actuator path—passes between the perimeter wall and the housing. In a preferred embodiment, the perimeter wall defines a flow path through the actuator—an interior actuator path—passing through the inside of the actuator. The inlet section of the fluid passageway preferably includes an expanded section for holding the actuator, and the exterior actuator path is located in the expanded section outside of the actuator.

The actuator includes means for permitting flow from the nozzle to the exterior actuator path. The means for permitting flow to the exterior actuator path preferably includes raised segments on the perimeter wall's interior surface for maintaining a space between perimeter wall's interior surface and the nozzle's exterior surface.

In a preferred embodiment, the actuator also includes means, disposed on the perimeter wall's outlet end, for permitting flow from the interior actuator path to the valving chamber. The means for permitting flow from the interior actuator path to the valving chamber preferably includes castellations on the perimeter wall's outlet end. In the preferred embodiments having an interior actuator path, the actuator preferably includes means, disposed within the perimeter wall, for restricting flow through the interior actuator path. This means for restricting flow preferably includes a transverse wall mounted to and within the perimeter wall, wherein the transverse wall defines at least one aperture. This means for restricting flow preferably forces a substantial portion of the flow to pass through the exterior actuator path. The means for permitting flow to the exterior actuator path preferably includes raised areas on the transverse wall, in order to prevent the tip of the nozzle from sealingly pressing against the transverse wall.

In an alternative embodiment of the actuator, the transverse wall does not include an aperture, and the actuator does not have an interior actuator path through which fluid may flow. The transverse wall in such an embodiment urges the flow around the inlet end of the perimeter wall to the exterior of the actuator.

The actuator structure of the present invention causes the volume surrounding the actuator to be flushed whenever fluid is injected into or drawn from the valve. Thus, for example, if blood is drawn from a patient through the valve according to the present invention, then the valve may be flushed of blood by injecting saline or anticoagulant, for example, through the valve. The actuator design of the present invention will cause the saline to flow through both the interior and exterior actuator paths, thereby causing the blood to be flushed out of the volume surrounding the actuator, as well as the interior of the actuator.

The actuator is preferably molded from a rigid thermoplastic material. The housing is also preferably made from two components separately molded from rigid thermoplastic material and then ultrasonically welded together. A preferred embodiment of the invention has, disposed on either the actuator's exterior surface or the expanded section of the fluid passageway's inlet section, means for centering the actuator in the inlet section. The actuator is preferably symmetrical so that the actuator's inlet and outlet ends are interchangeable. The process of manufacturing the valve is simplified by making the ends of the actuator interchangeable.

These and other features, aspects and advantages of the present invention will become better understood with regard to the following description taken in conjunction with the

3 accompanying drawings wherein are set forth, by way of illustration and example, certain embodiments of this invention.

DETAILED DESCRIPTION OF SPECIFIC EMBODIMENTS

Figure 1:
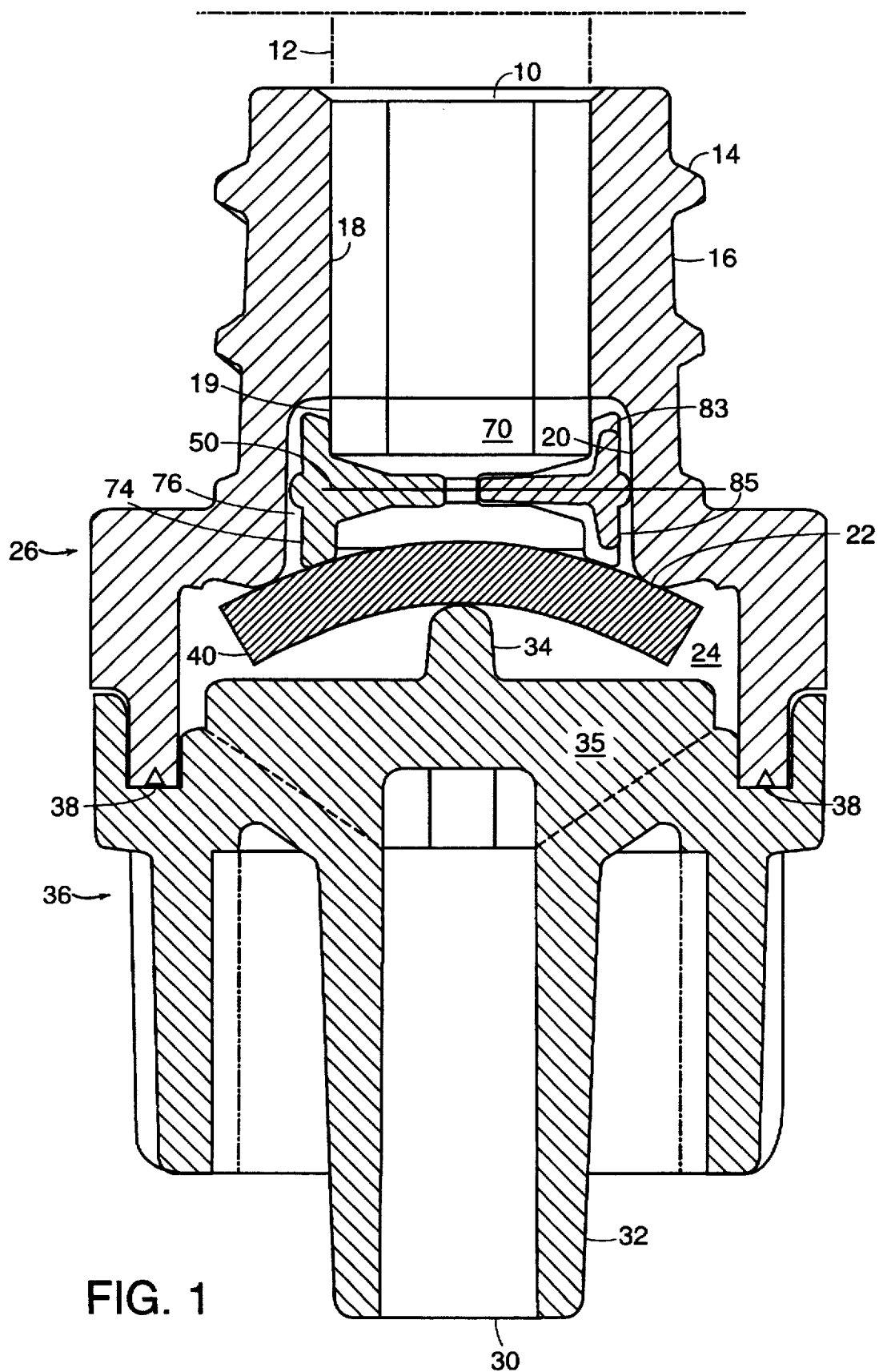
FIG. 1 shows a longitudinal sectional view of a valve according to one embodiment of the invention, wherein a nozzle has been inserted into the valve's inlet.

FIG. 1 shows a sectional view of a valve according to a preferred embodiment of the invention. The valve is assembled from four parts: an inlet housing component 26, an outlet housing component 36, a resilient, flexible disk 40, and an actuator 50. The inlet and outlet housing components 26, 36 are preferably attached to each other by ultrasonic welding along butt joint 38. The housing components define a fluid passageway passing from inlet 10 through a valving chamber 24 to outlet 30.

The inlet section 16 of the inlet housing component 26 is designed to accept a male Luer fitting 12 by tapering the inner surface 18 of the inlet section. In addition, the exterior of the inlet section 16 is provided with threads 14 so that a male Luer fitting 12 with a Luer lock—i.e., a collar having internal threads—may be locked into connection with the valve.

After the tapered section of the inlet's inner surface 18, the diameter of the fluid passage through the inlet housing component 26 widens to accommodate the actuator 50. Since the outer diameter of the actuator 50 is greater than the inner diameter of the tapered section's inner surface 18, the actuator 50 is prevented from falling out of the inlet end of the valve. At the boundary between the widened actuator section 20 of the fluid passageway and the valving chamber 24, a valve seat 22 is located on the inner surface of the inlet housing component 26. The disc 40, which is preferably made of a flexible, resilient material, such as silicone, is located in the valving chamber 24. The disc 40 is held against the valve seat 22 by a prong 34, which is mounted on ribs 35 extending into the fluid passageway. The prong 34 and the ribs 35 are integrally molded with the outlet housing component 36. The disc 40 may move side to side; the sideways movement of the disc 40 may be limited by placing axial ribs around the circumference of the valving chamber 24 in the manner described in U.S. Pat. Nos. 4,369,812 to Paradis and Kaleskas, and 5,190,067 to Paradis and Kotsifas.

4

The passage from the valving chamber 24 to the outlet 30 of the valve is defined by a wall 32, which in the depicted embodiment is shaped as a male Luer fitting. The outlet wall 32 may be surrounded by a Luer-lock collar 37 having threads (not shown) on its interior surface, so that the valve's outlet end may be securely connected may be connected to a female Luer fitting. Other outlet designs may be used depending on the intended use of the valve. For instance, the valve outlet wall 32 may be adapted in order to be welded to another rigid structure. The valve may also be integrally incorporated into a Y-joint site in a manner similar to that shown in U.S. Pat. Nos. 5,190,067 to Paradis and Kotsifas. The outlet may also be modified so that it comes out of the side of the valving chamber instead of the valving chamber's bottom (as shown in FIG. 1). In such a side-outlet configuration, which is similar to the check valve shown on the right side of FIG. 3B of U.S. Pat. No. 5,190,067 (referenced hereinabove), the outlet may be defined by the inlet housing component as well as the outlet housing component; i.e., the inlet housing component defines the outlet's top half, and the outlet housing component defines the outlet's bottom half.

The valve is normally closed and can function as a check valve. If the pressure at the inlet 10 is greater than the pressure at the outlet 30 by a certain amount (this pressure differential being commonly referred to as the cracking pressure), the disc 40 will separate from the valve seat 22, thereby permitting flow from the inlet 10 to the outlet 30. If it is desired to permit flow in the opposite direction (from what is normally the outlet 30 to what is normally the inlet 10), or if it desired to permit flow from the inlet 10 to the outlet 30 when the pressure differential between the inlet and the outlet is less than the cracking pressure, the valve may be actuated by a nozzle 12, which will cause the disk 40 to separate from the valve seat 22 when the nozzle is inserted into the valve. When the nozzle 12, which in FIG. 1 is a male Luer fitting, is inserted into the valve's inlet 10, it engages the actuator 50 and pushes the actuator towards the disc 40. The actuator 50, in turn, pushes on the disc 40, forcing the disc away from the valve seat 22. With the disc 40 held open by the nozzle 20 and the actuator 50, fluid may flow in either direction through the valve.

Figure 2A:
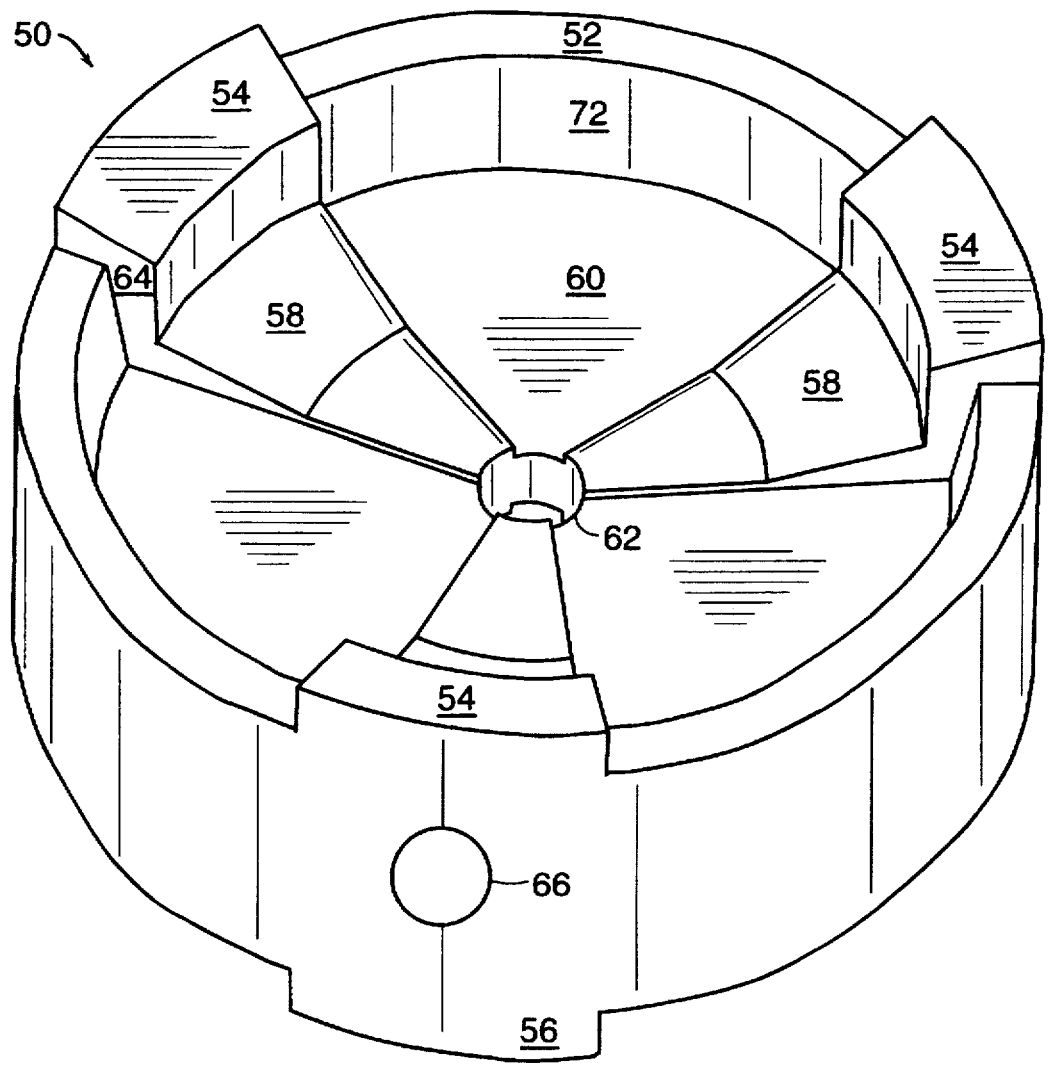
FIG. 2A shows a perspective view of the actuator used in the valve of FIG. 1.
Figure 3:
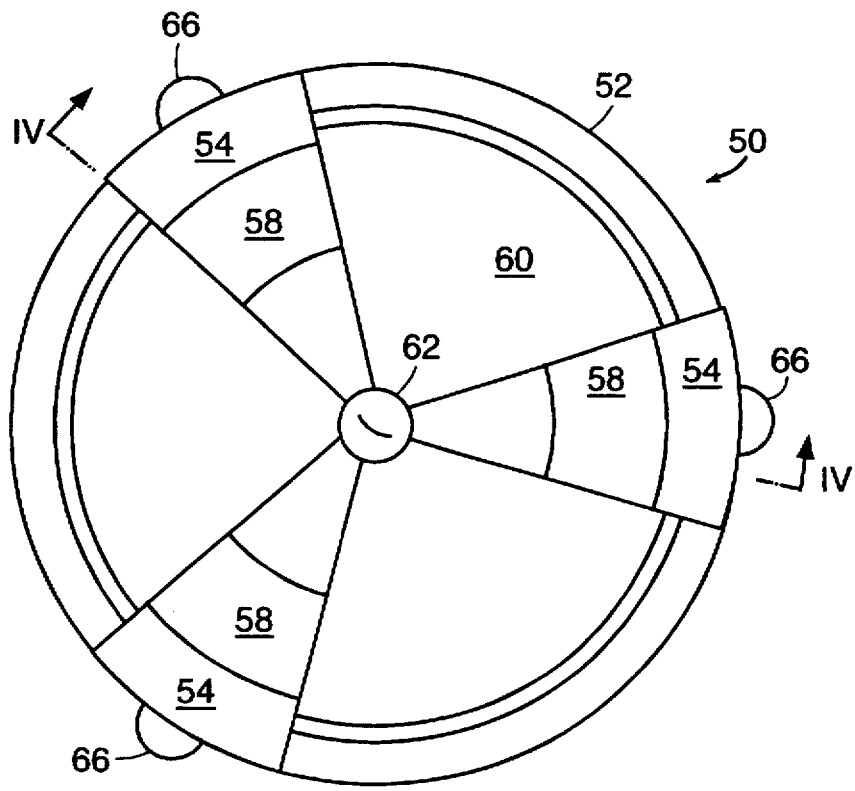
FIG. 3 shows a top view of the actuator of FIG. 2A.
Figure 4:
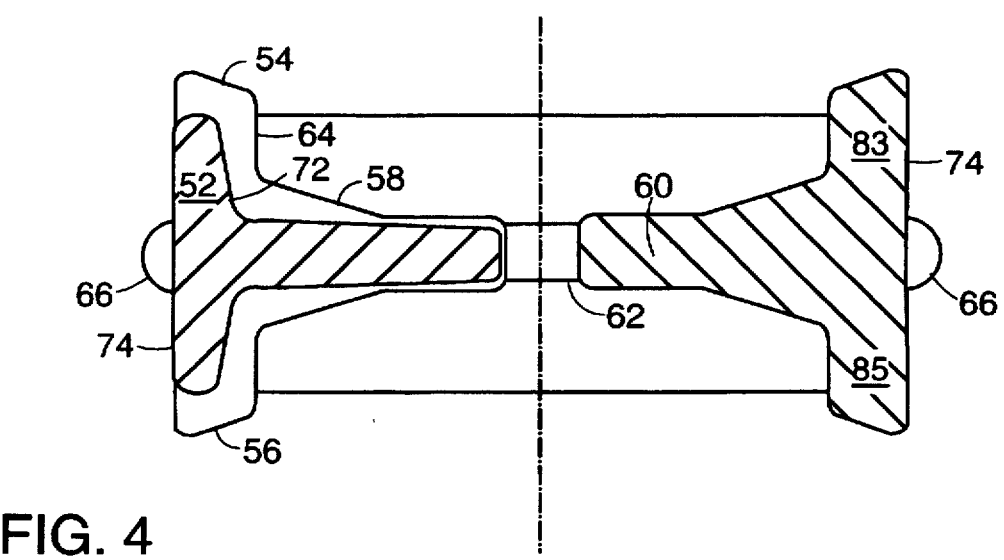
FIG. 4 shows a sectional view of the actuator of FIG. 3.

The actuator 50 is shown in greater detail in FIGS. 2A, 3 and 4. Like the inlet and outlet housing components 26, 36, the actuator is preferably molded from a rigid thermoplastic material, such as acrylic. The actuator 50 includes a perimeter wall 52, which is preferably concentrically aligned with the fluid passageway defined by the inlet housing component 26 and a transverse wall 60, which extends perpendicular to the perimeter wall 52 across the interior of the actuator. The transverse wall 60 defines an aperture 62, through which fluid may pass.

Castellations 56 located at the disc end 85 of the perimeter wall 52 ensure that fluid is able to flow from the aperture 62 between the perimeter wall 52 and the disc 40. Thus, the structure of the actuator ensures that fluid may flow through the interior actuator path: from the nozzle 12, through the aperture 62 defined by the transverse wall 60, between the perimeter wall's disc end 85 and the disc 40 through passages defined by the castellations 56, past the valve seat 22, into the valving chamber 24, and eventually to the valve's outlet 30. Fluid may also flow in the opposite direction through the interior actuator path.

As shown in FIG. 1, an annular volume 76 is defined around the actuator 50 by the outer surface 74 of the actuator and the inner surface 20 of the expanded section of the fluid passage between the inlet 10 and the valving chamber 24.

The actuator is provided with raised areas 58 (shown in FIGS. 2A, 3 and 4) on the side of the transverse wall 60 distal from the disc 40, in order to ensure that this annular volume 76 is flushed every time fluid is injected into or drawn from the valve. The raised areas 58 on the transverse wall 60 keep the nozzle's tip 70 separated from the transverse wall 60, so that fluid can flow between the nozzle tip 70 and the transverse wall 60 even when nozzle tip 70 is being forcefully urged towards the disc 40. Raised areas 64 on the inner surface 72 of the perimeter wall 52 keep the exterior surface 19 of the nozzle 12 separated from the inner surface 72 of the perimeter wall 52. The inner diameter of the perimeter wall 52 is preferably made sufficiently large so that it is greater than the outer diameter of all standard luer nozzle tips 70, so as to ensure that such a nozzle tip may be inserted, at least part way, into the interior of the actuator 50. In an alternative embodiment where the inner diameter of the perimeter wall is not larger than the outer diameter of the nozzle tip, the castellations 54 at the top of the actuator may serve to maintain a space between the top of the perimeter wall and the nozzle tip so that the nozzle tip does not sealingly butt against the top of the actuator.

Preferably, the actuator 50 is also provided with hemispherical centering pads 66 along its outer surface, in order to keep the actuator 50 centered in the expanded section of the fluid passage. Alternatively, axial ribs may be located on the interior surface 20 in the expanded section of the fluid passage in order to keep the actuator 50 centered.

Thus, the structure of the actuator ensures that fluid may also flow freely through the exterior actuator path: from the nozzle 12, between the nozzle's tip 70 and the transverse wall 60, around the inlet end 83 of the perimeter wall 52, through the annular passage 76 surrounding the actuator 50, past the valve seat 22, into the valving chamber 24, and eventually to the valve's outlet 30. Fluid may also flow in the opposite direction through the exterior actuator path.

Figure 2B:
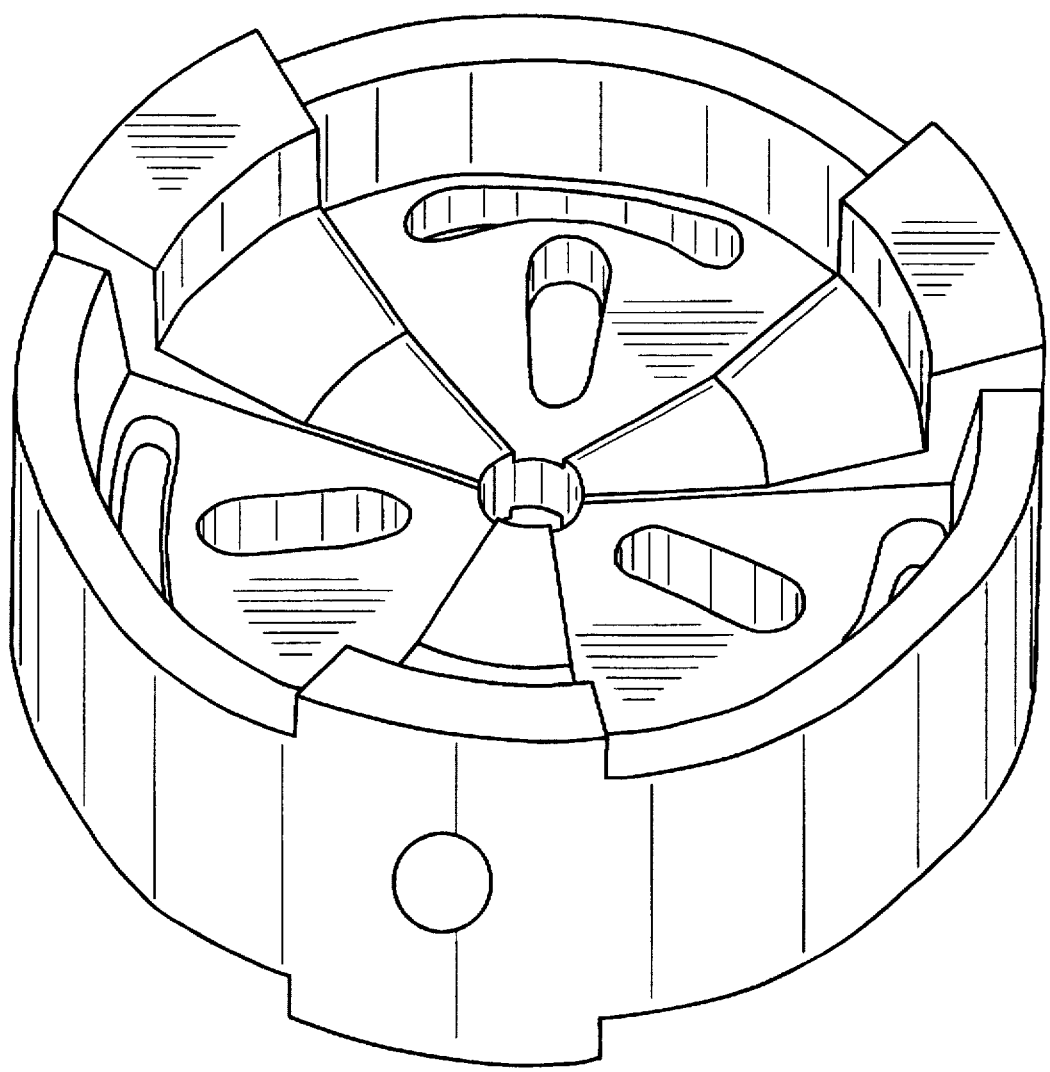
FIG. 2B shows a perspective view of an alternative actuator, showing alternative locations for apertures through the actuator's transverse wall.

Thus, the actuator 50 is provided with structures that ensure that flow may pass through both the interior and exterior actuator paths. The relative amount of flow that passes through each of the two paths depends on the resistance that each path creates on flow. A restriction is added to the interior actuator path in order to force a substantial amount of flow through the exterior actuator path; otherwise, only a relatively small amount of flow would pass through the exterior actuator path, since the interior actuator path is shorter than the exterior actuator path and, without the restriction, would also have a greater cross-sectional area than the exterior actuator path. This restriction is the transverse wall 60, through which the aperture 62 is defined. By changing the size of the aperture 62 through the transverse wall 60, or by changing the number of apertures through the transverse wall, the relative amounts of flow through the interior and exterior actuator paths can be adjusted. FIG. 2B shows some examples of where additional apertures may be added through the transverse wall 60.

It is desired to cause a substantial amount of flow to pass through both the interior and exterior actuator paths in order to ensure that the volume of the fluid passageway around the actuator 50 is thoroughly flushed each time fluid is injected into or drawn out of the valve. The number and size of the apertures through the transverse wall are accordingly chosen to achieve the desired balance of flow between the interior and exterior actuator paths.

The valve of the present invention may be used, for example, as a shunt in a patient through which blood may be drawn from the patient. A Luer-tipped syringe is inserted into the inlet 10 of the valve and, by the Luer tip 70 pressing on the actuator 50, the disc 40 is separated from the valve seat 22; blood may then be drawn through the valve from the outlet 30, which is attached to the patient, through the inlet 10 and into the syringe. After the desired amount of blood is drawn from the patient, the syringe is disconnected from the valve, which then automatically assumes its normally closed position. Some blood may be left in the valve and, in particular, around the actuator 50. Since the actuator 50 is on the inlet side of the disc 40, this blood may be exposed to atmosphere when the valve's inlet 10 is not connected to a male Luer fitting. In order to remove this blood, the valve may be flushed with saline or an anticoagulant. This is accomplished by using a second Luer-tipped syringe, which is filled with the saline or anticoagulant. The male Luer tip of the second syringe is inserted into the valve's inlet 10, and the saline or anticoagulant is forced out of the syringe through the valve. The actuator's design causes a substantial amount of the saline and anticoagulant to pass through both of the interior and exterior actuator paths.

Another advantage of the actuator design shown in the figures is that the actuator is able to accommodate a range of male Luer tip dimensions. It will be seen from FIG. 1 that, in the preferred embodiment of the valve, the tip 70 normally passes into the interior of the actuator 50 instead of butting against the actuator's top (as shown in FIG. 1). At some point, either the exterior surface 19 of the Luer fitting 12 will come into contact with the raised areas 64 on the inner surface 72 of the perimeter wall 52, or the bottom surface (as shown in FIG. 1) of the Luer fitting 12 will come into contact with the raised areas 58 on the transverse wall 60 or the castellations 54 at the perimeter wall's inlet end 83. At that point, the actuator 50 will start separating the disc 40 from the valve seat 22. Because of the range of when and where the Luer fitting 12 can come into contact with the actuator 50, the actuator is able to accommodate a range of male Luer dimensions. The presence of the transverse wall 60, along with the raised areas 58 on the transverse wall, prevents the Luer tip 70 from bottoming out on the disc 40.

The valve is preferably assembled in the following manner. The inlet housing component 26 is held so that the inlet end 10 is down and the valve-chamber end is up. The actuator 50 is then dropped into the expanded section 20 of the inlet housing component. Then the disc 40 is dropped on top of the actuator 50. The outlet housing component 36 is then placed on top of the inlet housing component 26 with the prong 34 touching the disc 40. The inlet and outlet housing components are then ultrasonically welded together. In order to facilitate this manufacturing process, the actuator 50 is preferably made symmetric so that it does not matter which end of the actuator is facing up when the actuator is dropped into the expanded section 20 of the inlet housing component 26 during the manufacturing process. Accordingly, the inlet end 83 of the perimeter wall 52 is also provided with castellations 54. Thus, a symmetric actuator has castellations at both ends and raised areas on both sides of the transverse wall. With the actuator 50 symmetrically designed in this way, it is unnecessary to orient the actuator before it is dropped into the inlet housing component 26.

Figure 5A:
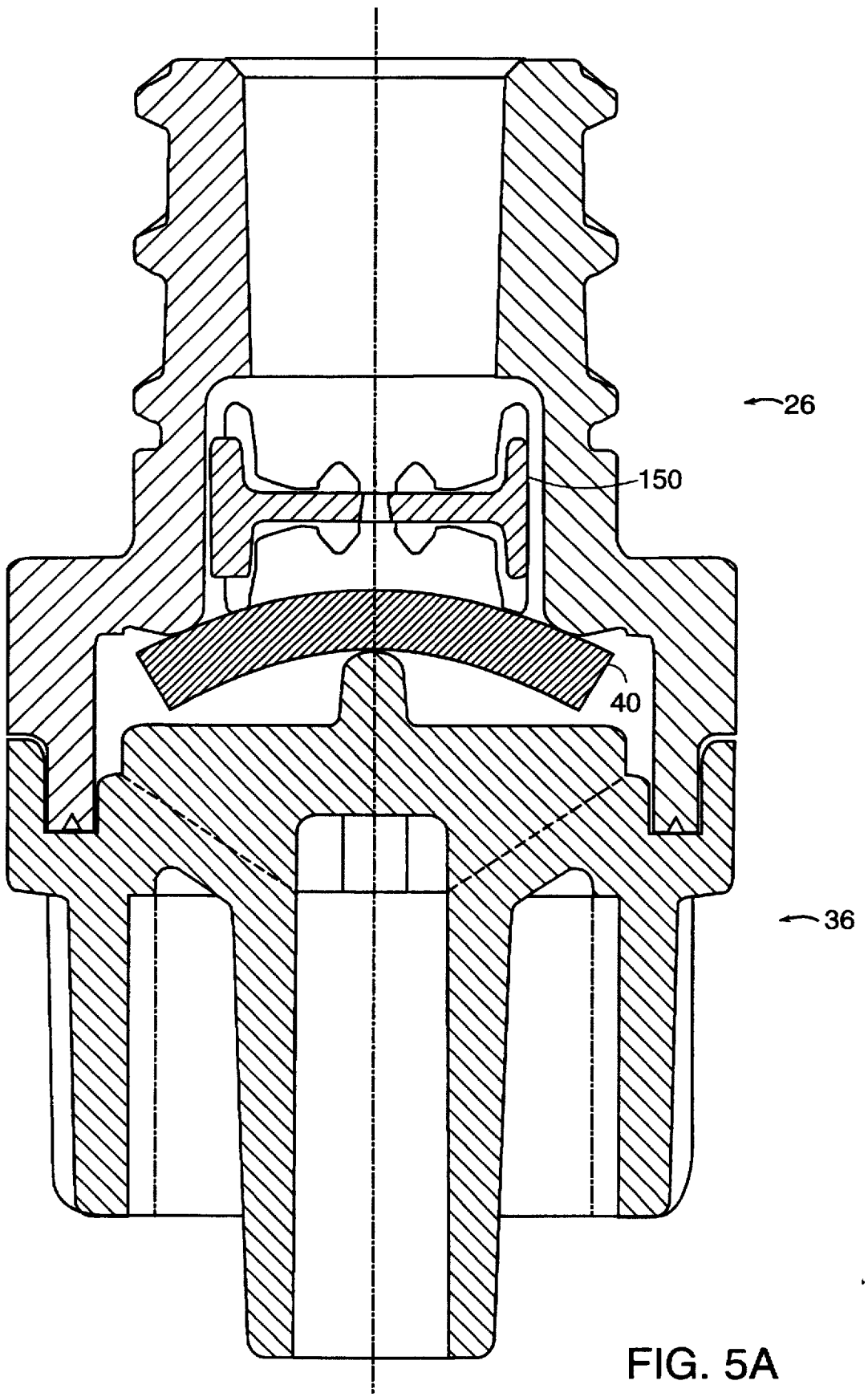
FIG. 5A shows a longitudinal section view of a valve according to an alternative embodiment of the invention.
Figure 5B:
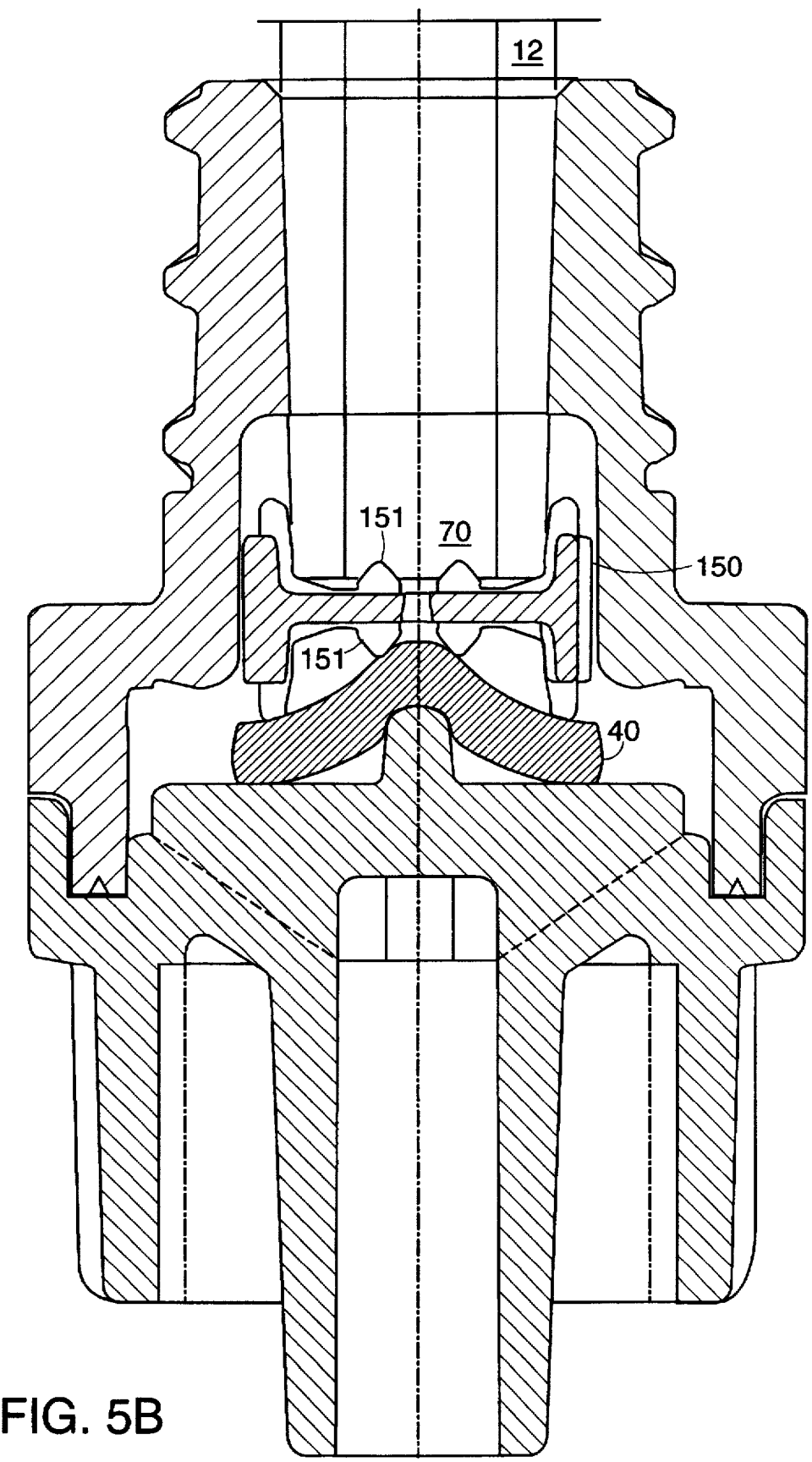
FIG. 5B shows the valve of FIG. 5A with a nozzle inserted into the valve's inlet.

FIGS. 5A–8 show an alternative embodiment of the valve. FIG. 5A shows a sectional view of a valve. Like the valve shown in FIG. 1, the valve shown in FIG. 5 is assembled from four parts: an inlet housing component 26, an outlet housing component 36, a resilient, flexible disk 40, and an actuator 150. FIG. 5B shows the valve of FIG. 5A with a nozzle 12 pushing the actuator 150 against the disk 40.

Protrusions 151 located on the transverse wall 160 (see FIGS. 6–8) around the clover-shaped aperture 162 ensure that the disk 40 cannot seal off the aperture 162. In order to make the actuator symmetric, these protrusions 151 are located on both sides of the transverse wall 160. Like the actuator shown in FIGS. 2A, 3 and 4, the actuator 150 shown in FIGS. 5A–8 also has castellations 154 on its top end and castellations 156 on its bottom end, so that no matter which way the actuator is placed in the valve during manufacturing, castellations on the outlet end of the actuator will permit flow between the actuator 150 and the disk 40. Likewise, the actuator 150 has raised areas 158 on both sides of the transverse wall 160 to ensure that, no matter what way the actuator 150 is placed in the valve, the nozzle tip 70 cannot sealingly butt against the transverse wall 160. Similarly, raised areas 164 on the interior of the perimeter wall 152 ensure that the outer diameter of the nozzle tip 70 is spaced away from the perimeter wall's inner surface. The ribs 167 on the perimeter wall's outer surface serve a purpose similar to the centering pads 66 discussed earlier; they keep the actuator centered in the fluid passageway. By keeping the actuator centered, the exterior actuator path may be kept sufficiently wide all the way around the actuator, and thus sufficient fluid may pass around the actuator to flush the annular volume around the actuator. If the actuator is off-center, it is difficult to flush that portion of the exterior actuator path where the path is constricted because the actuator is near the housing.

Figure 6:
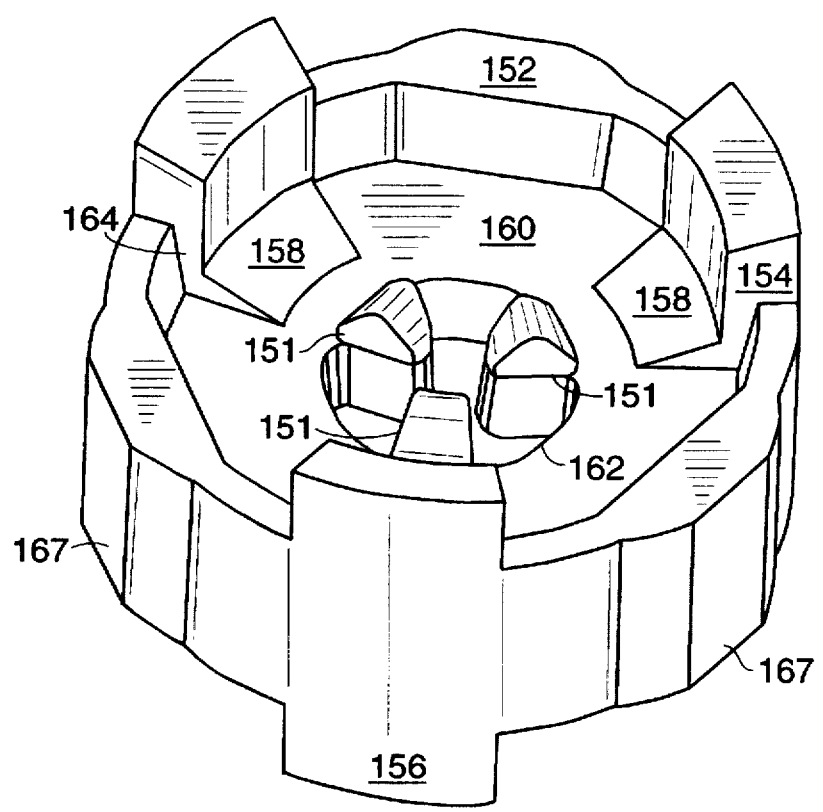
FIG. 6 shows a perspective view of the actuator used in the valve shown in FIG. 5A.
Figure 7:
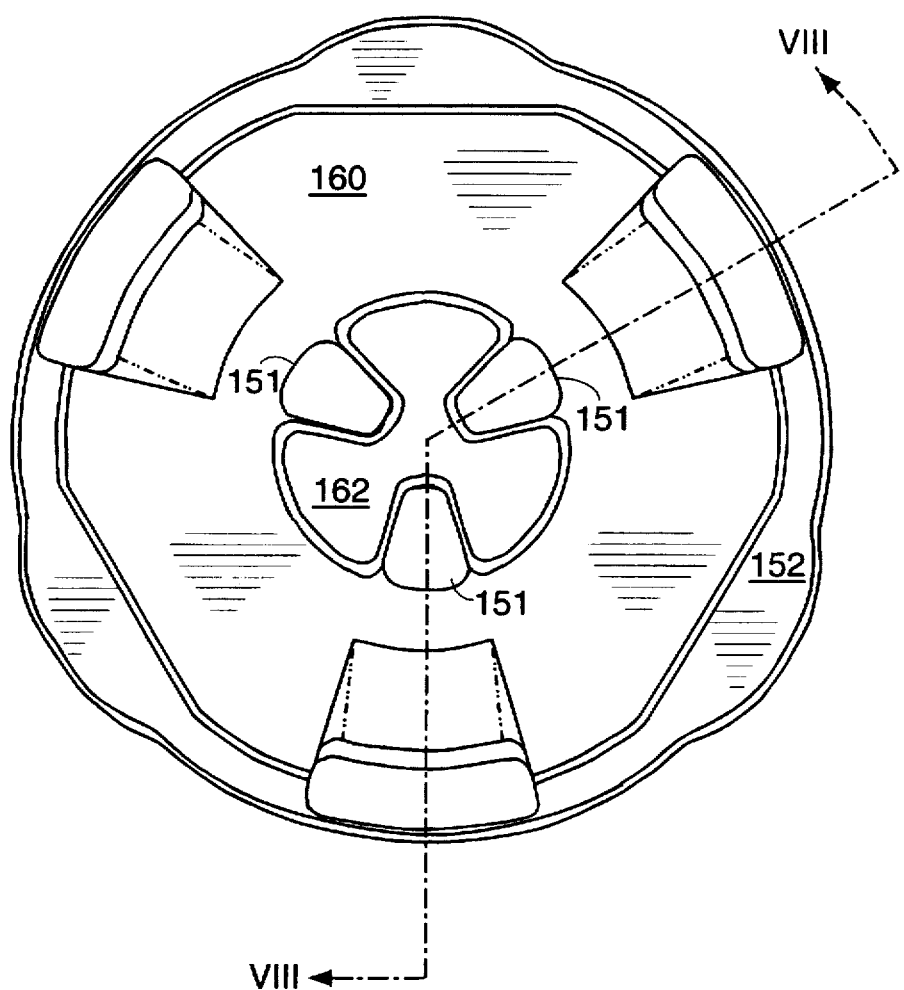
FIG. 7 shows a top view of the actuator shown in FIG. 6.
Figure 8:
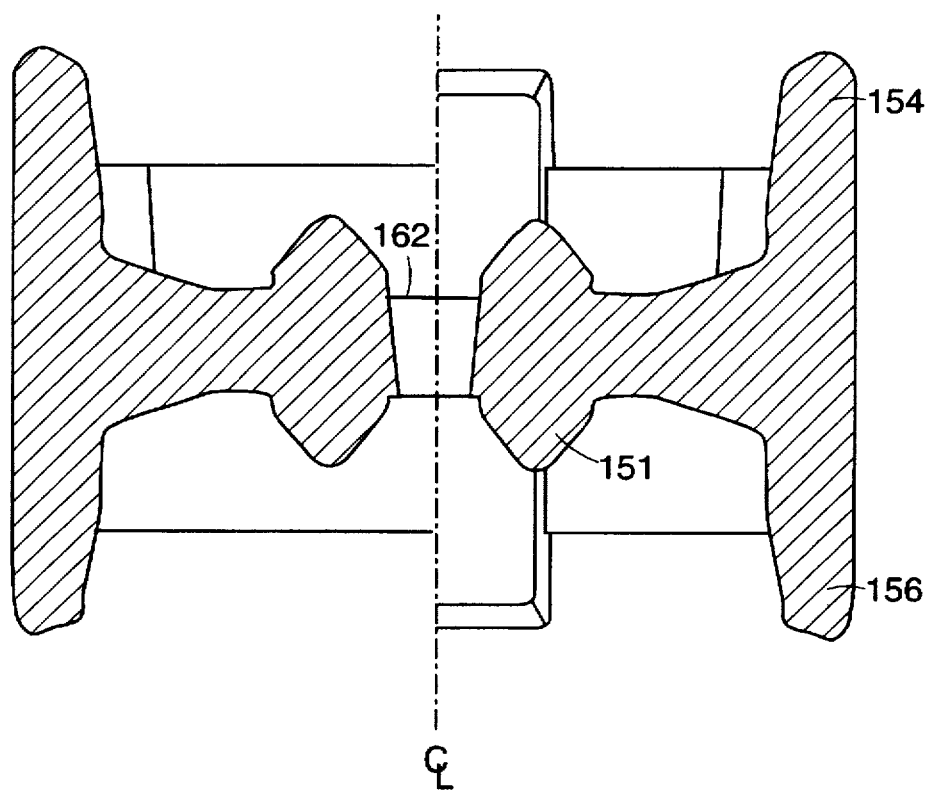
FIG. 8 shows a sectional view of the actuator shown in FIG. 7.
Figure 9:
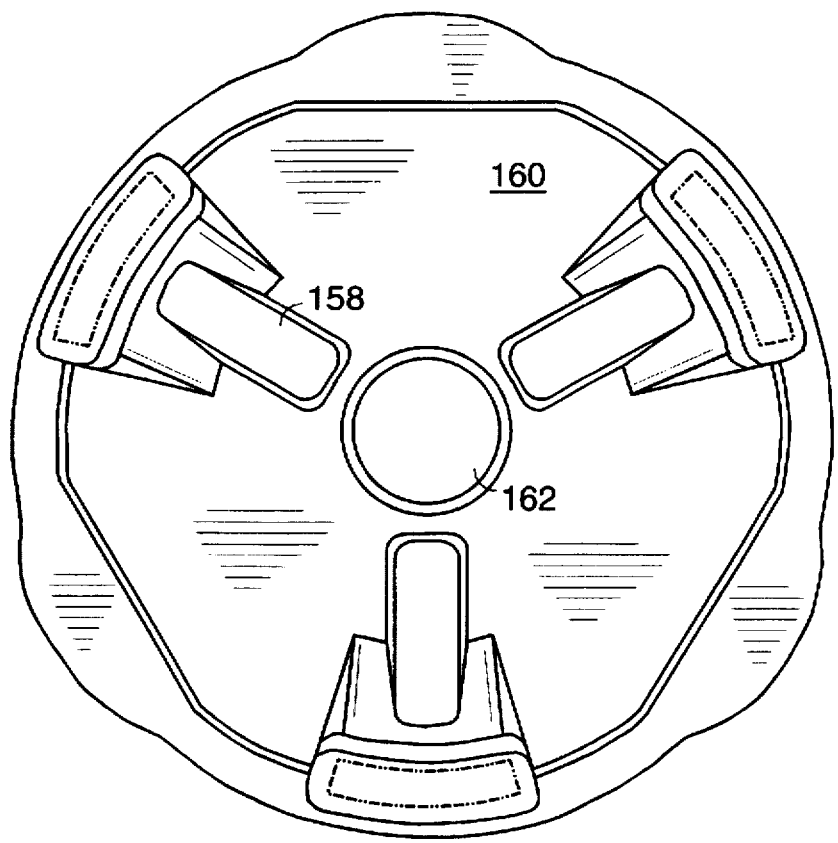
FIGS. 9–11 show top views of three alternative embodiments of the actuator.
Figure 10:
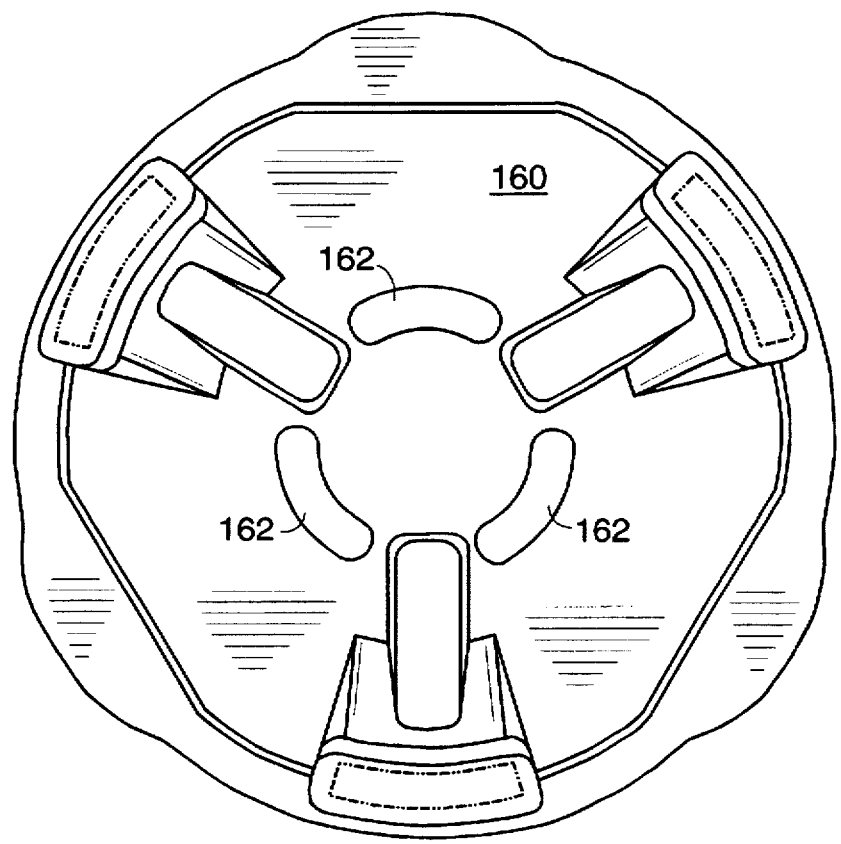

FIG. 9 shows a variation of the actuator shown in FIGS. 6–8. The FIG. 9 actuator has a circular aperture 162 through its transverse wall 160 and does not have protrusions (such as items 151 in FIG. 6). Raised areas 158 keep the nozzle tip separated from the transverse wall 160. FIG. 10 shows a variation of the FIG. 9 embodiment, wherein three separate arcuate apertures 162 are used instead of a single aperture.

Figure 11:
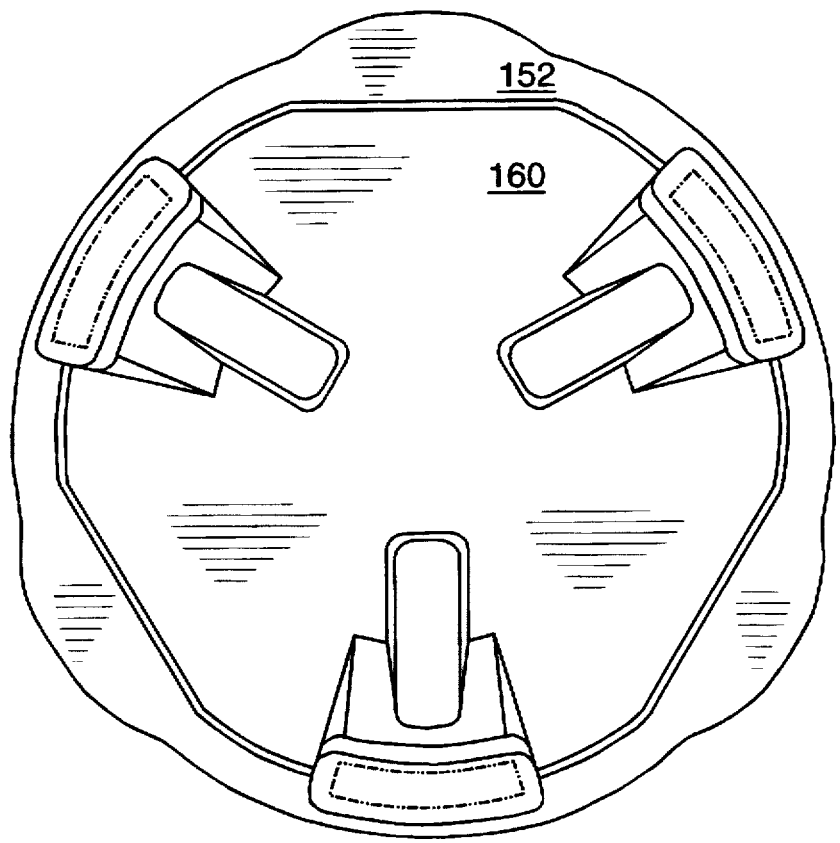

FIG. 11 shows another variation of the FIG. 9 actuator; in the FIG. 11 actuator, the transverse wall 160 has no apertures. In this embodiment, there is no internal actuator path for the fluid to pass through. The transverse wall 160 urges all the fluid to flow back around the nozzle tip and around the inlet end of the perimeter wall 152 to the exterior actuator path.

Although the invention has been described with reference to several preferred embodiments, it will be understood by one of ordinary skill in the art that various modifications can be made without departing from the spirit and the scope of the invention, as set forth in the claims hereinbelow. For example, the actuators shown in the figures may be used in the valve shown and described in U.S. Pat. No. 5,465,938 to Werge and Kotsifas in lieu of the actuator or plunger (item 24) shown in said patent.

I claim:

1. A normally closed valve that may be opened upon insertion of a nozzle, the valve comprising:

a housing including:

an inlet housing portion defining an inlet section of a fluid passageway, and an outlet housing portion defining an outlet section of the fluid passageway, the inlet and outlet housing portions being connected so as to permit fluid communication between the inlet and outlet sections of the fluid passageway, the housing further defining a valving chamber, the valving chamber forming a middle section of the fluid passageway between the inlet section and the outlet section;

an actuateable valve element, located in the valving chamber, that in a first position blocks flow through the passageway, and that in a second position permits flow through the passageway; and an actuator, disposed adjacent the actuateable valve element and the inlet section, for urging the actuateable valve element into the second position when the nozzle is inserted into the inlet section, the actuator including:

a perimeter wall, the perimeter wall having an inlet end disposed away from the valve element and an outlet end disposed towards the valve element, the perimeter wall defining an interior actuator path, and the perimeter wall and the housing defining an exterior actuator path, means for permitting flow from the nozzle to the exterior actuator path, wherein the means includes means for maintaining a space between the perimeter wall's interior surface and the nozzle's exterior surface, and means, disposed on the perimeter wall's outlet end, for permitting flow from the interior actuator path to the valving chamber.

2. A normally closed valve that may be opened upon insertion of a nozzle, the valve comprising:

a housing including:

an inlet housing portion defining an inlet section of a fluid passageway, wherein the inlet section is shaped to receive the nozzle, and an outlet housing portion defining an outlet section of the fluid passageway, the inlet and outlet housing portions being connected so as to permit fluid communication between the inlet and outlet sections of the fluid passageway, the housing further defining a valving chamber, the valving chamber forming a middle section of the fluid passageway between the inlet section and the outlet section;

an actuateable valve element, located in the valving chamber, that in a first position blocks flow through the passageway, and that in a second position permits flow through the passageway; and an actuator, disposed adjacent the actuateable valve element and the inlet section, for urging the actuateable valve element into the second position when the nozzle is inserted into the inlet section, the actuator including:

a perimeter wall, the perimeter wall having an inlet end disposed away from the valve element and an outlet end disposed towards the valve element, the perimeter wall defining an interior actuator path, and the perimeter wall and the housing defining an exterior actuator path, means for permitting flow from the nozzle to the exterior actuator path, means, disposed within the perimeter wall, for restricting flow through the interior actuator path, and means, disposed on the perimeter wall's outlet end, for permitting flow from the interior actuator path to the valving chamber.

3. A valve according to claim 2, further including a valve seat located on the housing in the valving chamber adjacent the actuateable valve element, such that, in the first position, the valve element rests against the valve seat, and in the second position, the actuateable valve element is spaced away from the valve seat, and wherein the actuateable valve element includes a flexible, resilient disk.

4. A valve according to claim 3, wherein the valve further includes means, connected to the outlet housing portion, for supporting the disk at the disk's center so as to urge the disk against the valve seat.

5. A valve according to claim 4, wherein the actuator is molded from a rigid thermoplastic material.

6. A valve according to claim 5, wherein the inlet and outlet housing portions are separately molded from rigid thermoplastic material and ultrasonically welded together.

7. A valve according to claim 6, wherein the inlet section of the fluid passageway is tapered to accept a male Luer tip as the nozzle.

8. A valve according to claim 7, wherein the inlet section includes an expanded section for holding the actuator, and wherein the exterior actuator path is located in the expanded section.

9. A valve according to claim 8, wherein the means for restricting flow includes a transverse wall mounted to and within the perimeter wall, wherein the transverse wall defines at least one aperture.

10. A valve according to claim 9, wherein the means for permitting flow to the exterior actuator path includes means mounted on the transverse wall for keeping the nozzle spaced from the transverse wall.

11. A valve according to claim 10, wherein the means for permitting flow to the exterior actuator path includes raised segments on the perimeter wall's interior surface for maintaining a space between perimeter wall's interior surface and the nozzle's exterior surface.

12. A valve according to claim 11, wherein the means for permitting flow from the interior actuator path to the valving chamber includes castellations on the perimeter wall's outlet end.

13. A valve according to claim 12, wherein the means for restricting flow forces a substantial portion of the flow to pass through the exterior actuator path.

14. A valve according to claim 13, further including means for centering the actuator in the inlet section.

15. A valve according to claim 14, wherein the means for centering the actuator in the inlet section includes raised areas disposed on the perimeter's exterior surface.

16. A valve according to claim 15, wherein the means for permitting flow to the exterior actuator path includes castellations on the perimeter wall's inlet end.

17. A valve according to claim 16, wherein the actuator is symmetrical so that the inlet end and the outlet end are interchangeable.

18. A valve according to claim 12, wherein the means for permitting flow to the exterior actuator path includes castellations on the perimeter wall's inlet end, and
wherein the actuator is symmetrical so that the inlet end and the outlet end are interchangeable.

19. A valve according to claim 2, wherein the means for restricting flow includes a transverse wall mounted to and within the perimeter wall, wherein the transverse wall defines at least one aperture,
wherein the means for permitting flow to the exterior actuator path includes means mounted on the transverse wall for keeping the nozzle spaced from the transverse wall, and
wherein the means for permitting flow from the interior actuator path to the valving chamber includes castellations on the perimeter wall's outlet end.

20. A valve according to claim 19, wherein the means for permitting flow to the exterior actuator path includes raised segments on the perimeter wall's interior surface for maintaining a space between perimeter wall's interior surface and the nozzle's exterior surface.

21. A valve according to claim 20, further including means, disposed on the transverse wall, for keeping the transverse wall spaced away from the valve element.

22. A valve according to claim 9, further including means, disposed on the transverse wall, for keeping the transverse wall spaced away from the disk.

23. An actuator for opening a valve element in a normally closed valve upon insertion of a nozzle into a valve input, the actuator comprising:
  a perimeter wall, the perimeter wall having an inlet end disposed away from the valve element and an outlet end disposed towards the valve element, the perimeter wall forming a barrier between an interior actuator path, located within the perimeter wall, and an exterior actuator path, located outside of the perimeter wall;
  means for permitting flow from the nozzle to the exterior actuator path, wherein the means includes means for maintaining a space between the perimeter wall's interior surface and the nozzle's exterior surface; and
  means, disposed on the perimeter wall's outlet end, for permitting flow from the interior actuator path past the valve element.

24. An actuator for opening a valve element in a normally closed valve upon insertion of a nozzle into the valve's input, the actuator comprising:
  a perimeter wall, the perimeter wall having an inlet end disposed away from the valve element and an outlet end disposed towards the valve element, the perimeter wall forming a barrier between an interior actuator path, located within the perimeter wall, and an exterior actuator path, located outside of the perimeter wall;
  means for permitting flow from the nozzle to the exterior actuator path;
  means, disposed within the perimeter wall, for restricting flow through the interior actuator path; and
  means, disposed on the perimeter wall's outlet end, for permitting flow from the interior actuator path past the valve element.

25. An actuator according to claim 24, wherein the means for restricting flow includes a transverse wall mounted to and within the perimeter wall, wherein the transverse wall defines at least one aperture.

26. An actuator according to claim 25, wherein the means for permitting flow to the exterior actuator path includes means mounted on the transverse wall for keeping the nozzle spaced from the transverse wall.

27. An actuator according to claim 26, wherein the means for permitting flow to the exterior actuator path includes raised segments on the perimeter wall's interior surface for maintaining a space between perimeter wall's interior surface and the nozzle's exterior surface.

28. An actuator according to claim 27, wherein the means for permitting flow from the interior actuator path past the valve element includes castellations on the perimeter wall's outlet end.

29. An actuator according to claim 28, wherein the means for restricting flow forces a substantial portion of the flow to pass through the exterior actuator path.

30. An actuator according to claim 29, further including raised areas disposed on the perimeter wall's exterior surface.

31. An actuator according to claim 30, wherein the means for permitting flow to the exterior actuator path includes castellations on the perimeter wall's inlet end.

32. An actuator according to claim 31, wherein the actuator is symmetrical so that the inlet end and the outlet end are interchangeable.

33. A normally closed valve that may be opened upon insertion of a nozzle, the valve comprising:

a housing including:
an inlet housing portion defining an inlet section of a fluid passageway, and
an outlet housing portion defining an outlet section of the fluid passageway, the inlet and outlet housing portions being connected so as to permit fluid communication between the inlet and outlet sections of the fluid passageway,
the housing further defining a valving chamber, the valving chamber forming a middle section of the fluid passageway between the inlet section and the outlet section;
an actuateable valve element, located in the valving chamber, that in a first position blocks flow through the passageway, and that in a second position permits flow through the passageway; and
an actuator, separably moveable with respect to the actuateable valve element and disposed adjacent the actuateable valve element and the inlet section, for urging the actuateable valve element into the second position, when the nozzle is inserted into the inlet section, the actuator including:
a perimeter wall, the perimeter wall having an inlet end disposed away from the valve element and an outlet end disposed towards the valve element, the perimeter wall and the housing defining an exterior actuator path,
means for permitting flow from the nozzle to the exterior actuator path, and
means, located within and attached to the perimeter wall, for urging flow from the nozzle to the exterior path.

34. A valve according to claim 33, further including a valve seat located on the housing in the valving chamber adjacent the actuateable valve element, such that, in the first position, the valve element rests against the valve seat, and in the second position, the actuateable valve element is spaced away from the valve seat,
wherein the actuateable valve element includes a flexible, resilient disk, wherein the valve further includes means, connected to the outlet housing portion, for supporting the disk at the disk's center so as to urge the disk against the valve seat, and
wherein the inlet section includes an expanded section for holding the actuator, and wherein the exterior actuator path is located in the expanded section.

35. A normally closed valve that may be opened upon insertion of a nozzle, the valve comprising:
a housing including
an inlet housing portion defining an inlet section of a fluid passageway, wherein the inlet section is shaped to receive the nozzle, and
an outlet housing portion defining an outlet section of the fluid passageway, the inlet and outlet housing portions being connected so as to permit fluid communication between the inlet and outlet sections of the fluid passageway,
the housing further defining a valving chamber, the valving chamber forming a middle section of the fluid passageway between the inlet section and the outlet section,
an actuateable valve element, located in the valving chamber, that in a first position blocks flow through the passageway, and that in a second position permits flow through the passageway; and
an actuator, separably moveable with respect to the actuateable valve element and disposed adjacent the actuateable valve element and the inlet section, for urging the actuateable valve element into the second position, when the nozzle is inserted into the inlet section, the actuator including:
a perimeter wall, the perimeter wall having an inlet end disposed away from the valve element and an outlet end disposed towards the valve element, the perimeter wall and the housing defining an exterior actuator path,
means for permitting flow from the nozzle to the exterior actuator path, and
means, located within the perimeter wall, for urging flow from the nozzle to the exterior path, wherein the means includes a transverse wall mounted to and within the perimeter wall.

36. A valve according to claim 35, wherein the transverse wall defines at least one aperture, so as to permit flow through an interior actuator path, which is defined by the perimeter wall.

37. A valve according to claim 35, wherein the means for permitting flow to the exterior actuator path includes means mounted on the transverse wall for keeping the nozzle spaced from the transverse wall.

38. A valve according to claim 37, wherein the means for permitting flow to the exterior actuator path includes raised segments on the perimeter wall's interior surface for maintaining a space between the perimeter wall's interior surface and the nozzle's exterior surface.

39. An actuator for opening a valve element in a normally closed valve upon engagement by a nozzle into a valve input, the actuator comprising:
a perimeter wall, the perimeter wall having an inlet end disposed away from the valve element and an outlet end disposed towards the valve element, the perimeter wall having an interior and an exterior;
a transverse wall, mounted to and within the perimeter wall, for urging flow from the nozzle past the interior of the perimeter wall around the inlet end of the perimeter wall; and
means for maintaining a space between the nozzle and the transverse wall so as to permit flow from the nozzle to the inlet end of the perimeter wall.

40. An actuator according to claim 39, further including raised segments on the perimeter wall's interior for maintaining a space between perimeter wall and the nozzle.

41. An actuator according to claim 40, further including raised areas disposed on the perimeter's exterior surface.

42. An actuator according to claim 41, wherein the actuator is symmetrical so that the inlet end and the outlet end are interchangeable.

43. A normally closed valve that may be opened upon insertion of a nozzle, the valve comprising:
a housing including:
an inlet housing portion defining an inlet section of a fluid passageway, and
an outlet housing portion defining an outlet section of the fluid passageway, the inlet and outlet housing portions being connected so as to permit fluid communication between the inlet and outlet sections of the fluid passageway,
the housing further defining a valving chamber, the valving chamber forming a middle section of the fluid passageway between the inlet section and the outlet section;
an actuateable valve element, located in the valving chamber, that in a first position blocks flow through the passageway, and that in a second position permits flow through the passageway;

an actuator for urging the actuateable valve element into the second position, when the nozzle is inserted into the inlet section, the actuator including a perimeter wall, the perimeter wall and the housing defining an exterior actuator path;

means for permitting flow from the nozzle to the exterior actuator path, wherein the means includes means for maintaining a space between perimeter wall's interior surface and the nozzle's exterior surface; and means, located in the exterior actuator path, for centering the actuator in the inlet section.

44. A valve according to claim 43, wherein the means for centering the actuator in the inlet section includes raised areas disposed on the perimeter wall's exterior surface.

* * * * *